(12) United States Patent
Wang et al.

(10) Patent No.: US 12,257,251 B2
(45) Date of Patent: Mar. 25, 2025

(54) USE OF FAK INHIBITOR IN PREPARATION OF DRUG FOR TREATING TUMORS HAVING NRAS MUTATION

(71) Applicant: INXMED (NANJING) CO., LTD., Nanjing (CN)

(72) Inventors: Zaiqi Wang, Shanghai (CN); Jiangwei Zhang, Shanghai (CN); Jun Jiang, Beijing (CN)

(73) Assignee: INXMED (NANJING) CO., LTD., Nanjing (CN)

(*) Notice: Subject to any disclaimer, the term of this patent is extended or adjusted under 35 U.S.C. 154(b) by 0 days.

(21) Appl. No.: 18/350,303

(22) Filed: Jul. 11, 2023

(65) Prior Publication Data

US 2023/0364088 A1     Nov. 16, 2023

Related U.S. Application Data

(63) Continuation of application No. 17/777,769, filed as application No. PCT/CN2020/129350 on Nov. 17, 2020.

(30) Foreign Application Priority Data

Nov. 18, 2019   (CN) .......................... 201911128794.9

(51) Int. Cl.
*A61K 31/506*     (2006.01)
*A61K 31/4439*    (2006.01)
(Continued)

(52) U.S. Cl.
CPC ........ *A61K 31/506* (2013.01); *A61K 31/4439* (2013.01); *A61K 31/5377* (2013.01);
(Continued)

(58) Field of Classification Search
CPC .............. A61K 31/506; A61K 31/4439; A61K 31/5377; A61K 45/06; A61K 31/337;
(Continued)

(56) References Cited

U.S. PATENT DOCUMENTS

2016/0264574 A1   9/2016 Stogniew et al.
2016/0346282 A1  12/2016 Pachter et al.
(Continued)

FOREIGN PATENT DOCUMENTS

CA      3125058 A1    7/2020
CN    102292322 A    12/2011
(Continued)

OTHER PUBLICATIONS

Lee et al., FAK signaling in human cancer as a target for therapeutics, Pharmacology & Therapeutics, 2015, 146, pp. 132-149 (Year: 2015).*

(Continued)

*Primary Examiner* — Savitha M Rao
*Assistant Examiner* — Andrew P Lee
(74) *Attorney, Agent, or Firm* — K&L Gates LLP

(57) ABSTRACT

A use of a FAK inhibitor in the preparation of a drug for preventing and/or treating tumors having an NRAS mutation. A method for treating tumors that have experienced an NRAS mutation, which comprises administering an effective dose of a FAK inhibitor to an individual. A FAK inhibitor for treating tumors having an NRAS mutation. The FAK inhibitor is BI853520, defactinib, GSK2256098, PF-00562271, VS-4718 or a pharmaceutically acceptable salt thereof.

15 Claims, 7 Drawing Sheets

(51) Int. Cl.
  A61K 31/5377 (2006.01)
  A61K 45/06 (2006.01)
  A61P 1/00 (2006.01)
  A61P 17/00 (2006.01)
  A61P 19/04 (2006.01)
  A61P 35/00 (2006.01)
(52) U.S. Cl.
  CPC ............... *A61K 45/06* (2013.01); *A61P 1/00* (2018.01); *A61P 17/00* (2018.01); *A61P 19/04* (2018.01); *A61P 35/00* (2018.01)
(58) Field of Classification Search
  CPC .......... A61K 31/444; A61P 1/00; A61P 17/00; A61P 19/04; A61P 35/00
  See application file for complete search history.

(56) References Cited

U.S. PATENT DOCUMENTS

| | | | |
|---|---|---|---|
| 2018/0177788 | A1 | 6/2018 | Pachter et al. |
| 2023/0000867 | A1 | 1/2023 | Wang et al. |
| 2023/0145356 | A1 | 5/2023 | Wang et al. |
| 2024/0024319 | A1 | 1/2024 | Wang et al. |

FOREIGN PATENT DOCUMENTS

| | | |
|---|---|---|
| CN | 108289892 A | 7/2018 |
| CN | 111565742 A | 8/2020 |
| EP | 4101453 A1 | 12/2022 |
| WO | 2010058032 A2 | 5/2010 |
| WO | 2012136829 A1 | 10/2012 |
| WO | 2015120289 A1 | 8/2015 |
| WO | 2017004192 A1 | 1/2017 |
| WO | 2018115380 A1 | 6/2018 |
| WO | 2020202005 A1 | 10/2020 |
| WO | 2021048339 A1 | 3/2021 |
| WO | 2021104454 A1 | 6/2021 |
| WO | 2021154929 A1 | 8/2021 |
| WO | 2021155764 A1 | 8/2021 |

OTHER PUBLICATIONS

Bastin et al., Salt Selection and Optimisation Procedures for Pharmaceutical New Chemical Entities, Organic Process Research & Development, 2000, 4, pp. 427-435 (Year: 2000).*
Kurenova et al., A FAK scaffold inhibitor disrupts FAK and VEGFR-3 signaling and blocks melanoma growth by targeting both tumor and endothelial cells, 2014, 13(16), pp. 2542-2553 (Year: 2014).*
Signorelli et al., Cobimetinib: A Novel MEK Inhibitor for Metastatic Melanoma, Annals of Pharmacology, 2017, 51(2), pp. 146-153 (Year: 2017).*
Zhang et al., "Gain-of-Function RHOA Mutatations Promote Focal Adhesion Kinase Activation and Dependency in Diffuse Gastric Cancer," Cancer Discovery (2020) vol. 10, pp. 288-305.
Fredericks et al., "The role of RAS effectors in BCR/ABL induced chronic myelogenous leukemia," Front Med (2013) vol. 7, No. 4, pp. 452-461.
Cuiffo et al., "Palmitoylation of oncogenic NRAS is essential for leukemogenesis," Blood (2010) vol. 115, No. 17, pp. 3598-3605.
Hirt et al., "Efficacy of the highly selective focal adhesion kinase inhibitor BI 853520 in adenocarcinoma xenograft models is linked to a mesenchymal tumor phenotype," Oncogenesis (2018) vol. 7, Article 21, 11 pages.
Lee et al., "FAK signaling in human cancer as a target for therapeutics," Pharmacology & Therapeutics (2015) vol. 146, pp. 132-149.
Parikh et al., "Oncogenic NRAS, KRAS, and HRAS Exhibit Different Leukemogenic Potentials in Mice," Cancer Res (2007) vol. 67, No. 15, pp. 7139-7146.
Tiede et al., "The FAK inhibitor BI 853520 exerts anti-tumor effects in breast cancer," Oncogenesis (2018) vol. 7, Article 73, 19 pages.
Zhang et al., "Bcr-Abl Efficiently Induces a Myeloproliferative Disease and Production of Excess Interleukin-3 and Granulocyte-Macrophase Colony-Stimulating Factor in Mice: A Novel Model for Chronic Myelogenous Leukemia," Blood (1998) vol. 92, No. 10, pp. 3829-3840.
Zhang et al., "Efficacy of focal adhesion kinase inhibition in non-small cell lung cancer with oncogenically activated MAPK pathways," British Journal of Cancer (2016) vol. 115, pp. 203-211.
Zhang et al., "A Simple Statistical Parameter for Use in Evaluation and Validation of High Throughput Screening Assays," Journal of Biomolecular Screening (1999) vol. 4, No. 2, pp. 67-73.
[No Author Listed] "Congratulations! INSTEC FAK inhibitors are clinically approved in China," Press release, Medicine Guanlan Report, WuXi AppTec published on Dec. 19, 2019, 3 pages.
Abuhammad et al., Inhibition of the protein arginine methyltransferase PRMT5 overcomes resistance to CDK4-inhibition in melanoma, Pigment Cell Melanoma Res (2018) vol. 31, p. 125, Abstract from SMR Congress 2017.
Beierle et al., "TAE226 inhibits human neuroblastoma cell survival," Cancer Investigation (2008) vol. 26, pp. 145.151.
Doi et al., "Phase I Study of the Focal Adhesion Kinase Inhibitor BI 853520 in Japanese and Taiwanese Patients with Advanced or Metastatic Solid Tumors," Targeted Oncology (2019) vol. 14, pp. 57-65.
Hirata et al., "Intravital Imaging Reveals How BRAF Inhibition Generates Drug-Tolerant Microenvironments with High Integrin Beta1/FAK Signaling," Cancer Cell (2015) vol. 27, pp. 574-588.
[No Author Listed] "Yingshi Announces Clinical Collaboration with Merck & Co., Inc to Evaluate IN10018 in Combination with Pembrolizumab," Press Release retrieved from cnmobile.prnasia.com, Oct. 26, 2023, Chinese with English translation.
[No Author Listed] Machine translation of WO 2021155764 (Year: 2021).
[No Author Listed] Press Release—"Congratulations! Yingshi BioFAK inhibitor was approved for clinical use in China," retrieved from xueqiu.com/9766314542/137684324, (2019) 3 pages.
[No Author Listed] Press Release: "Yingshi Biological FAK Inhibitor IN10018 Phase I Clinical Trial Approved in China," PR Newswire, Dec. 20, 2019, retrieved from prnasia.com/story/268783-1.shtml, Chinese with English translation.
Dragoj et al., "Targeting CXCR4 and FAK reverses doxorubicin resistance and suppresses invasion in non-small cell lung carcinoma," Cell Oncol (2017) vol. 40, pp. 47-62.
Golubovskaya et al., "Disruption of focal adhesion kinase and p53 interaction with small molecule compound R2 reactivated p53 and blocked tumor growth," BMC Cancer (2013) vol. 13, Article 342, 14 pages.
Golubovskaya et al., "MiR-138 and MiR-135 Directly Target Focal Adhesion Kinase , Inhibit Cell Invasion , and Increase Sensitivity to Chemotherapy in Cancer Cells," Anticancer Agents Med Chem (2014) vol. 14, No. 1, pp. 18-28.
Gupta et al., "Salts of Therapeutic Agents: Chemical, Physicochemical, and Biological Considerations," Molecules (2018) vol. 23, Article 1719, 15 pages.
He et al., "Studies on the Role of Focal Adhesion Kinase in Disease," Acta Neuropharmacologica (2021) vol. 11, No. 3, pp. 50-64. Chinese with English abstract.
International Search Report and Written Opinion issued in PCT/CN2022/110234, mailed Nov. 3, 2022, Chinese with English translation.
International Search Report issued in PCT/CN2021/074371, mailed on Mar. 30, 2021.
Kurenova et al., "The Small Molecule Chloropyramine Hydrochloride (C4) Targets the Binding Site of Focal Adhesion Kinase and Vascular Endothelial Growth Factor Receptor 3 and Suppresses Breast Cancer Growth in vivo," J Med Chem (2009) vol. 52, No. 15, pp. 4716-4724.
Laszlo et al., "The FAK inhibitor BI 853520 inhibits sphereoid formation and orthotopic tumor growth in malignant pleural mesothelioma," Journal of Molecular Medicine (2019) vol. 97, pp. 231-242.

(56) References Cited

OTHER PUBLICATIONS

Li et al., "The impact of Pegylated liposomal doxorubicin in recurrent ovarian cancer: an updated meta-analysis of randomized clinical trials," Journal of Ovarian Research (2021) vol. 14, Article 42, 12 pages.

Mohanty et al., "FAK-targeted and combination therapies for the treatment of cancer: an overview of phase I and II clinical trials," Expert Opinion on Investigational Drugs (2020) vol. 29, No. 4, pp. 399-409.

Solomon et al., "Clinical Pharmacology of Liposomal Anthacyclines: Focus on Pegylated Liposomal Doxorubicin," Clinical Lyphoma & Myeloma (2008) vol. 8, No. 1, pp. 21-32.

Tavora et al., "Endothelial-cell FAK targeting sensitizes tunours to DNA-damaging therapy," Nature (2014) vol. 514, pp. 112-116 and Methods pages.

Yu et al., "Connexin 32 affects doxorubicin resistance in hepatocellular carcinoma cells mediated by Src/FAK signaling pathway," Biomedicine & Pharmacotherapy (2017) vol. 95, pp. 1844-1852.

Zhang et al., "Focal Adhesion Kinase (FAK) Inhibition Synergizes with KRAS G12C Inhibitors in Treating Cancer through the Regulation of the FAK-YAP Signaling," Advanced Science (2021) vol. 8, Article e2100250, 15 pages.

International Search Report and Written Opinion issued in PCT/CN2020/129350, mailed Feb. 22, 2021, Chinese with English translation.

de Jonge, Maja J A et al. "Phase I Study of BI 853520, an Inhibitor of Focal Adhesion Kinase, in Patients with Advanced or Metastatic Nonhematologic Malignancies." Targeted Oncology vol. 14, 1 (2019): 43-55.

Office Action mailed in corresponding Canadian Patent Application No. 3,158,585 dated Aug. 5, 2024.

\* cited by examiner

USE OF FAK INHIBITOR IN PREPARATION OF DRUG FOR TREATING TUMORS HAVING NRAS MUTATION

CROSS REFERENCE TO RELATED APPLICATIONS

The present application is a continuation of U.S. application Ser. No. 17/777,769. U.S. application Ser. No. 17/777,769 is a national application of PCT/CN2020/129350 filed on Nov. 17, 2020 which claims the priority of the Chinese Patent Application No. 201911128794.9 filed on Nov. 18, 2019. The Chinese Patent Application No. 201911128794.9 is incorporated herein by reference as part of the disclosure of the present application.

FIELD OF THE INVENTION

The present disclosure belongs to the field of pharmaceutical chemistry, and particularly relates to use of an FAK inhibitor in the manufacture of a medicament for treating tumors having an NRAS mutation.

BACKGROUND OF THE INVENTION

FAK, also known as protein tyrosine kinase 2 (PTK2), is a non-receptor tyrosine kinase and a key component of the focal adhesion complex. FAK plays an important role in mediating integrin and growth factor signaling to regulate invasion, proliferation and survival of tumor cells. FAK is widely expressed and evolutionarily conserved. Studies in the past 20 years have shown that FAK is overexpressed in a variety of solid tumors, and the expression level is negatively correlated with tumor prognosis. Recent studies have also shown that FAK plays an important role in regulating the tumor microenvironment, which suggests that FAK plays an important role in adaptive resistance to immunotherapy and anti-tumor therapy. Both in vitro and in vivo preclinical studies have shown that blocking FAK has anti-tumor effects. However, the inhibitory activity of FAK inhibitors against tumors varies widely.

BI853520 is a FAK inhibitor. In human tumor CDX (Cell line-Derived Xenograft) mice model of 37 different tumors, BI853520 has showed different anti-tumor activities, and its TGI (tumor growth inhibition) span from 0 to 107%. Inhibiting tumor growth by using BI853520 in a more targeted manner is a technical problem to be solved urgently in this field.

SUMMARY OF THE INVENTION

In one aspect, the present disclosure provides use of a FAK inhibitor in the manufacture of a medicament for treating a tumor having an NRAS mutation.

Optionally, the FAK inhibitor is BI853520, defactinib, GSK2256098, PF-00562271, VS-4718 or a pharmaceutically acceptable salt thereof.

Alternatively, the FAK inhibitor is BI853520 or a pharmaceutically acceptable salt thereof, especially BI853520 tartrate.

The BI 853520 has the following structure:

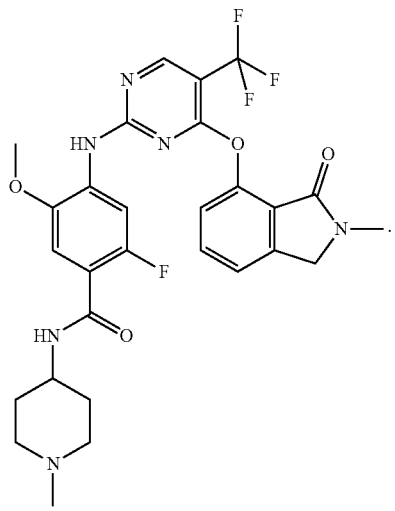 [SMILES: COc1cc(C(=O)NC2CCN(C)CC2)c(F)cc1Nc1ncc(C(F)(F)F)c(Oc2cccc3c2C(=O)N(C)C3)n1]

Optionally, the medicament is used in combination with an effective amount of a second therapeutic agent.

Optionally, the medicament is used in combination with radiotherapy or cell therapy.

Optionally, the tumor is Hodgkin's lymphoma, non-Hodgkin's lymphoma, non-small cell lung cancer, small cell lung cancer, hepatocellular carcinoma, cholangiocarcinoma, myelodysplastic syndrome, acute lymphoblastic leukemia, acute myeloid leukemia, chronic myeloid leukemia, thyroid cancer, glioma, colon cancer, rectal cancer, colorectal cancer, ovarian cancer, bladder cancer, prostate cancer, breast cancer, liposarcoma, fibrosarcoma, rhabdomyosarcoma, leiomyosarcoma, angiosarcoma, neuroblastoma, renal cell carcinoma, head and neck cancer, stomach cancer, esophageal cancer, gastroesophageal junction cancer, thymic cancer, pancreatic cancer, endometrial cancer, cervical cancer, melanoma, skin cancer, germ cell carcinoma, nasopharyngeal carcinoma, oropharyngeal carcinoma or laryngeal carcinoma; further the tumor is acute myeloid leukemia, melanoma, thyroid carcinoma, colorectal carcinoma, esophageal carcinoma, hepatocellular carcinoma, ovarian carcinoma, fibrosarcoma or cholangiocarcinoma.

Optionally, the second therapeutic agent is one or more selected from chemotherapeutic agents, targeted therapeutic agents and immunotherapy agents.

Optionally, the second therapeutic agent is one or more selected from the group consisting of nimustine, carmustine, lomustine, temozolomide, cyclophosphamide, isocyclophosphamide, glyfosfin, doxifluridine, Furtulon, fluorouraeil, mercaptopurine, azathioprine, tioguanine, floxuridine, tegafur, gemcitabine, decitabine, carmofur, hydroxyurea, methotrexate, UFT, capecitabine, ancitabine, thiotepa, actinomycin D, adriamycin, liposomal doxorubicin, daunorubicin, epirubicin, mitomycin, pingyangmycin, pirarubicin, valrubicin, idarubicin, irinotecan, harringtonine, camptothecin, hydroxycamptothecine, topotecan, vinorelbine (navelbine), taxol, taxotere, hycamtin, vinblastine, vincristine, vindesine, vindesine sulfate, vincaleukoblastine, teniposide, etoposide, elemene, atamestane, anastrozole, aminoglutethimide, letrozole, formestane, megestrol, tamoxifen, asparaginase, carboplatin, cisplatin, dacarbazine, oxaliplatin, eloxatin, Eloxatin(Ke Bo Ao Sha), mitoxantrone, procarbazine, docetaxel, gefitinib, erlotinib, icotinib, afatinib, osimertinib, crizotinib, ceritinib, alectinib, lapatinib, everolimus, palbociclib, ribociclib, apatinib, regorafenib, sorafenib, sunitinib, temsirolimus, lenvatinib, pazopanib, Alectinib(A Lei Ti Ni), axitinib, cabozantinib, trametinib, binimetinib, vemurafenib, dabrafenib, Cobimetinib(Ka Bi Ti Ni), vandetanib, bortezomib, palbociclib, lenalidomide, ixazomib, imatinib, dasatinib, bosutinib, ponatinib, ibrutinib, idelalisib, belinostat, romidepsin, vorinostat, olaparib, niraparib, denosumab, vismodegib, sonidegib, rucaparib, brigatinib, bicalutamide, enzalutamide, abiraterone, abemaciclib, apalutamide, aflibercept, azacitidine, bleomycin, chlorambucil, cytarabine, Asparaginase(Tian Dong Xian An Mei), epothilone, fludarabine, flutamide, mechlorethamine, paclitaxel, pemetrexed, raltitrexed, necitumumab, bevacizumab, ramucirumab, Ado-trastuzumab, pertuzumab, cetuximab, panitumumab, alirocumab, durvalumab, nimotuzumab, daratumumab, atezolizumab, sintilimab, toripalimab, camrelizumab, tislelizumab, durvalumab, nivolumab, and pembrolizumab.

Optionally, the second therapeutic agent is selected from the group consisting of decitabine, gemcitabine, cisplatin, carboplatin, oxaliplatin, adriamycin, liposomal doxorubicin, taxol, docetaxel, trametinib, binimetinib, cobimetinib, durvalumab, atezolizumab, sintilimab, toripalimab, camrelizumab, tislelizumab, nivolumab, and pembrolizumab.

Optionally, the second therapeutic agent is docetaxel, liposomal doxorubicin, cobimetinib, pembrolizumab, or decitabine.

Optionally, the second therapeutic agent is cobimetinib.

In another aspect, the present disclosure also provides a method of treating a tumor having an NRAS mutation comprising administering to an individual an effective amount of a FAK inhibitor.

Optionally, the FAK inhibitor is BI853520 or defactinib, GSK2256098, PF-00562271, VS-4718 or a pharmaceutically acceptable salt thereof, alternatively, the FAK inhibitor is BI853520 or a pharmaceutically acceptable salt thereof, especially BI853520 tartrate.

Optionally, the method further comprises administering to the individual an effective amount of a second therapeutic agent.

Optionally, the method further includes radiotherapy or cell therapy.

Optionally, the tumor is Hodgkin's lymphoma, non-Hodgkin's lymphoma, non-small cell lung cancer, small cell lung cancer, hepatocellular carcinoma, cholangiocarcinoma, myelodysplastic syndrome, acute lymphoblastic leukemia, acute myeloid leukemia, chronic myeloid leukemia, thyroid cancer, glioma, colon cancer, rectal cancer, colorectal cancer, ovarian cancer, bladder cancer, prostate cancer, breast cancer, liposarcoma, fibrosarcoma, rhabdomyosarcoma, leiomyosarcoma, angiosarcoma, neuroblastoma, renal cell carcinoma, head and neck cancer, stomach cancer, esophageal cancer, gastroesophageal junction cancer, thymic cancer, pancreatic cancer, endometrial cancer, cervical cancer, melanoma, skin cancer, germ cell carcinoma, nasopharyngeal carcinoma, oropharyngeal carcinoma or laryngeal carcinoma; further the tumor is acute myeloid leukemia, melanoma, thyroid carcinoma, colorectal carcinoma, esophageal carcinoma, hepatocellular carcinoma, ovarian carcinoma, fibrosarcoma or cholangiocarcinoma.

Optionally, the second therapeutic agent is one or more selected from chemotherapeutic agents, targeted therapeutic agents and immunotherapy agents.

Optionally, the second therapeutic agent is one or more selected from the group consisting of nimustine, carmustine, lomustine, temozolomide, cyclophosphamide, isocyclophosphamide, glyfosfin, doxifluridine, Furtulon, fluorouraeil, mercaptopurine, azathioprine, tioguanine, floxuridine, tegafur, gemcitabine, decitabine, carmofur, hydroxyurea, methotrexate, UFT, capecitabine, ancitabine, thiotepa, actinomycin D, adriamycin, liposomal doxorubicin, daunorubicin, epirubicin, mitomycin, pingyangmycin, pirarubicin, valrubicin, idarubicin, irinotecan, harringtonine, camptothecin, hydroxycamptothecine, topotecan, vinorelbine (navelbine), taxol, taxotere, hycamtin, vinblastine, vincristine, vindesine, vindesine sulfate, vincaleukoblastine, teniposide, etoposide, elemene, atamestane, anastrozole, aminoglutethimide, letrozole, formestane, megestrol, tamoxifen, asparaginase, carboplatin, cisplatin, dacarbazine, oxaliplatin, eloxatin, Eloxatin(Ke Bo Ao Sha), mitoxantrone, procarbazine, docetaxel, gefitinib, erlotinib, icotinib, afatinib, osimertinib, crizotinib, ceritinib, alectinib, lapatinib, everolimus, palbociclib, ribociclib, apatinib, regorafenib, sorafenib, sunitinib, temsirolimus, lenvatinib, pazopanib, Alectinib(A Lei Ti Ni), axitinib, cabozantinib, trametinib, binimetinib, vemurafenib, dabrafenib, Cobimetinib(Ka Bi Ti Ni), vandetanib, bortezomib, palbociclib, lenalidomide, ixazomib, imatinib, dasatinib, bosutinib, ponatinib, ibrutinib, idelalisib, belinostat, romidepsin, vorinostat, olaparib, niraparib, denosumab, vismodegib, sonidegib, rucaparib, brigatinib, bicalutamide, enzalutamide, abiraterone, abemaciclib, apalutamide, aflibercept, azacitidine, bleomycin, chlorambucil, cytarabine, Asparaginase(Tian Dong Xian An Mei), epothilone, fludarabine, flutamide, mechlorethamine, paclitaxel, pemetrexed, raltitrexed, necitumumab, bevacizumab, ramucirumab, Ado-trastuzumab, pertuzumab, cetuximab, panitumumab, alirocumab, durvalumab, nimotuzumab, daratumumab, atezolizumab, sintilimab, toripalimab, camrelizumab, tislelizumab, durvalumab, nivolumab, and pembrolizumab.

Optionally, the second therapeutic agent is selected from the group consisting of decitabine, gemcitabine, cisplatin, carboplatin, oxaliplatin, adriamycin, liposomal doxorubicin, taxol, docetaxel, trametinib, binimetinib, cobimetinib, durvalumab, atezolizumab, sintilimab, toripalimab, camrelizumab, tislelizumab, nivolumab, and pembrolizumab.

Optionally, the second therapeutic agent is docetaxel, liposomal doxorubicin, cobimetinib, pembrolizumab, or decitabine.

Optionally, the second therapeutic agent is cobimetinib.

Optionally, the second therapeutic agent is administered simultaneously, alternately or sequentially.

Optionally, the FAK inhibitor and radiotherapy or cell therapy are performed simultaneously, alternately or sequentially.

In yet another aspect, the present disclosure provides a FAK inhibitor for the treatment of a tumor having an NRAS mutation.

Optionally, the FAK inhibitor is BI853520, defactinib, GSK2256098, PF-00562271, VS-4718 or a pharmaceutically acceptable salt thereof, alternatively, the FAK inhibitor is BI853520 or a pharmaceutically acceptable salt thereof, especially BI853520 tartrate.

Optionally, the FAK inhibitor is further used in combination with an effective amount of a second therapeutic agent.

Optionally, the FAK inhibitor is further used in combination with radiotherapy or cell therapy.

Optionally, the tumor is Hodgkin's lymphoma, non-Hodgkin's lymphoma, non-small cell lung cancer, small cell lung cancer, hepatocellular carcinoma, cholangiocarcinoma, myelodysplastic syndrome, acute lymphoblastic leukemia, acute myeloid leukemia, chronic myeloid leukemia, thyroid cancer, glioma, colon cancer, rectal cancer, colorectal cancer, ovarian cancer, bladder cancer, prostate cancer, breast cancer, liposarcoma, fibrosarcoma, rhabdomyosarcoma, leiomyosarcoma, angiosarcoma, neuroblastoma, renal cell carcinoma, head and neck cancer, stomach cancer, esophageal cancer, gastroesophageal junction cancer, thymic cancer, pancreatic cancer, endometrial cancer, cervical cancer, melanoma, skin cancer, germ cell carcinoma, nasopharyngeal carcinoma, oropharyngeal carcinoma or laryngeal carcinoma; further the tumor is acute myeloid leukemia, melanoma, thyroid carcinoma, colorectal carcinoma, esophageal carcinoma, hepatocellular carcinoma, ovarian carcinoma, fibrosarcoma or cholangiocarcinoma.

Optionally, the second therapeutic agent is one or more selected from chemotherapeutic agents, targeted therapeutic agents and immunotherapy agents.

Optionally, the second therapeutic agent is one or more selected from the group consisting of nimustine, carmustine, lomustine, temozolomide, cyclophosphamide, isocyclophosphamide, glyfosfin, doxifluridine, Furtulon, fluorouraeil, mercaptopurine, azathioprine, tioguanine, floxuridine, tegafur, gemcitabine, decitabine, carmofur, hydroxyurea, methotrexate, UFT, capecitabine, ancitabine, thiotepa, actinomycin D, adriamycin, liposomal doxorubicin, daunorubicin, epirubicin, mitomycin, pingyangmycin, pirarubicin, valrubicin, idarubicin, irinotecan, harringtonine, camptothecin, hydroxycamptothecine, topotecan, vinorelbine (navelbine), taxol, taxotere, hycamtin, vinblastine, vincristine, vindesine, vindesine sulfate, vincaleukoblastine, teniposide, etoposide, elemene, atamestane, anastrozole, aminoglutethimide, letrozole, formestane, megestrol, tamoxifen, asparaginase, carboplatin, cisplatin, dacarbazine, oxaliplatin, eloxatin, Eloxatin(Ke Bo Ao Sha), mitoxantrone, procarbazine, docetaxel, gefitinib, erlotinib, icotinib, afatinib, osimertinib, crizotinib, ceritinib, alectinib, lapatinib, everolimus, palbociclib, ribociclib, apatinib, regorafenib, sorafenib, sunitinib, temsirolimus, lenvatinib, pazopanib, Alectinib(A Lei Ti Ni), axitinib, cabozantinib, trametinib, binimetinib, vemurafenib, dabrafenib, Cobimetinib(Ka Bi Ti Ni), vandetanib, bortezomib, palbociclib, lenalidomide, ixazomib, imatinib, dasatinib, bosutinib, ponatinib, ibrutinib, idelalisib, belinostat, romidepsin, vorinostat, olaparib, niraparib, denosumab, vismodegib, sonidegib, rucaparib, brigatinib, bicalutamide, enzalutamide, abiraterone, abemaciclib, apalutamide, aflibercept, azacitidine, bleomycin, chlorambucil, cytarabine, Asparaginase(Tian Dong Xian An Mei), epothilone, fludarabine, flutamide, mechlorethamine, paclitaxel, pemetrexed, raltitrexed, necitumumab, bevacizumab, ramucirumab, Ado-trastuzumab, pertuzumab, cetuximab, panitumumab, alirocumab, durvalumab, nimotuzumab, daratumumab, atezolizumab, sintilimab, toripalimab, camrelizumab, tislelizumab, durvalumab, nivolumab, and pembrolizumab.

Optionally, the second therapeutic agent is selected from the group consisting of decitabine, gemcitabine, cisplatin, carboplatin, oxaliplatin, adriamycin, liposomal doxorubicin, taxol, docetaxel, trametinib, binimetinib, cobimetinib, durvalumab, atezolizumab, sintilimab, toripalimab, camrelizumab, tislelizumab, nivolumab, and pembrolizumab.

Optionally, the second therapeutic agent is docetaxel, liposomal doxorubicin, cobimetinib, pembrolizumab, or decitabine.

Optionally, the second therapeutic agent is cobimetinib.

Definition

The following terms and symbols used in this application have the meanings set forth below unless the context dictates otherwise.

The term "FAK inhibitor" as used herein refers to a potent inhibitor of FAK, which may be suitable for mammals, particularly humans.

The term "NRAS" as used herein refers to an oncogene that is a member of the RAS oncogene family which also includes two other genes: KRAS and HRAS. These genes play important roles in cell division, cell differentiation and apoptosis.

The term "NRAS mutation" as used herein means that when a pathogenic mutation occurs in the NRAS gene, the N-Ras protein encoded by it will be in a state of continuous activation, resulting in uncontrolled cell proliferation and tumor formation.

The term "treating" as used herein refers to the administration of one or more drugs, particularly a FAK inhibitor described herein, especially BI853520 or a pharmaceutically acceptable salt thereof, to an individual with a disease or symptoms of said disease, to cure, alleviate, reduce, alter, remedy, ameliorate, improve or affect the disease or the symptoms of the disease. In some embodiments, the disease is a tumor or cancer. In further embodiments, the disease is a cancer or tumor having an NRAS mutation.

The term "tumor" as used herein refers to an abnormal lesion formed by abnormally clonal proliferation of cells of local tissues which lose the normal regulation on their growth at the gene level under the action of various tumorigenic factors. Examples include, but are not limited to: Hodgkin's lymphoma, non-Hodgkin's lymphoma, non-small cell lung cancer, small cell lung cancer, hepatocellular carcinoma, cholangiocarcinoma, myelodysplastic syndrome, acute lymphoblastic leukemia, acute myeloid leukemia, chronic myeloid leukemia, thyroid cancer, glioma, colon cancer, rectal cancer, colorectal cancer, ovarian cancer, bladder cancer, prostate cancer, breast cancer, liposarcoma, fibrosarcoma, rhabdomyosarcoma, leiomyosarcoma, angiosarcoma, neuroblastoma, renal cell carcinoma, head and neck cancer, stomach cancer, esophageal cancer, gastroesophageal junction cancer, thymic cancer, pancreatic cancer, endometrial cancer, cervical cancer, melanoma, skin cancer, germ cell carcinoma, nasopharyngeal carcinoma, oropharyngeal carcinoma or laryngeal carcinoma; further the tumors are acute myeloid leukemia, melanoma, thyroid carcinoma, colorectal carcinoma, esophageal carcinoma, hepatocellular carcinoma, ovarian carcinoma, fibrosarcoma and cholangiocarcinoma.

As used herein, the term "individual" refers to mammals and non-mammals. Mammals means any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "individual" does not denote a particular age or sex. In some embodiments, the individual is a human.

As used herein, the term "pharmaceutically acceptable" means non-toxic, biologically tolerable and suitable for administration to an individual.

As used herein, the term "pharmaceutically acceptable salt" refers to an acid addition salt of BI853520 that is non-toxic, biologically tolerable and suitable for administration to an individual. The "pharmaceutically acceptable salt" includes, but are not limited to, acid addition salts formed by BI853520 with an inorganic acid, such as hydrochloride, hydrobromide, carbonate, bicarbonate, phosphate, sulfate, sulfite, nitrate, and the like; and acid addition salts formed by BI853520 with an organic acid, such as formate, acetate, malate, maleate, fumarate, tartrate, succinate, citrate, lactate, methanesulfonate, p-toluenesulfonate, 2-hydroxyethanesulfonate, benzoate, salicylate, stearate, and salts with alkane-dicarboxylic acid of formula HOOC—$(CH_2)_n$—COOH (wherein n is 0-4), etc. In some embodiments, the salt is a tartrate salt.

In addition, a pharmaceutically acceptable acid addition salt may be produced by dissolving the free base in a suitable solvent and treating the solution with an acid, in accordance with conventional procedures for preparing acid addition salts from basic compounds. Those skilled in the art can determine, without undue experimentation, a variety of synthetic methods, which are used to prepare non-toxic pharmaceutically acceptable acid addition salts.

As used herein, the term "effective amount" refers to an amount sufficient to generally bring about a beneficial effect in an individual. The effective amount of the compounds of the present disclosure may be ascertained by conventional methods (such as modeling, dose escalation studies or clinical trials), and by taking into consideration conventional influencing factors (such as the mode of administration, the pharmacokinetics of the compound, the severity and course of the disease, the individual's medical history, the individual's health status and the individual's response to drugs).

The term "second therapeutic agent" as used herein refers to one or more drugs used to prevent and/or treat diseases. In some embodiments, the second therapeutic agent is one or more selected from chemotherapeutic agents, targeted therapeutic agents and immunotherapeutic agents. In some embodiments, the second therapeutic agent is one or more selected from the group consisting of nimustine, carmustine, lomustine, temozolomide, cyclophosphamide, isocyclophosphamide, glyfosfin, doxifluridine, Furtulon, fluorouraeil, mercaptopurine, azathioprine, tioguanine, floxuridine, tegafur, gemcitabine, decitabine, carmofur, hydroxyurea, methotrexate, UFT, capecitabine, ancitabine, thiotepa, actinomycin D, adriamycin, liposomal doxorubicin, daunorubicin, epirubicin, mitomycin, pingyangmycin, pirarubicin, valrubicin, idarubicin, irinotecan, harringtonine, camptothecin, hydroxycamptothecine, topotecan, vinorelbine (navelbine), taxol, taxotere, hycamtin, vinblastine, vincristine, vindesine, vindesine sulfate, vincaleukoblastine, teniposide, etoposide, elemene, atamestane, anastrozole, aminoglutethimide, letrozole, formestane, megestrol, tamoxifen, asparaginase, carboplatin, cisplatin, dacarbazine, oxaliplatin, eloxatin, Eloxatin(Ke Bo Ao Sha), mitoxantrone, procarbazine, docetaxel, gefitinib, erlotinib, icotinib, afatinib, osimertinib, crizotinib, ceritinib, alectinib, lapatinib, everolimus, palbociclib, ribociclib, apatinib, regorafenib, sorafenib, sunitinib, temsirolimus, lenvatinib, pazopanib, Alectinib(A Lei Ti Ni), axitinib, cabozantinib, trametinib, binimetinib, vemurafenib, dabrafenib, Cobimetinib(Ka Bi Ti Ni), vandetanib, bortezomib, palbociclib, lenalidomide, ixazomib, imatinib, dasatinib, bosutinib, ponatinib, ibrutinib, idelalisib, belinostat, romidepsin, vorinostat, olaparib, niraparib, denosumab, vismodegib, sonidegib, rucaparib, brigatinib, bicalutamide, enzalutamide, abiraterone, abemaciclib, apalutamide, aflibercept, azacitidine, bleomycin, chlorambucil, cytarabine, Asparaginase(Tian Dong Xian An Mei), epothilone, fludarabine, flutamide, mechlorethamine, paclitaxel, pemetrexed, raltitrexed, necitumumab, bevacizumab, ramucirumab, Ado-trastuzumab, pertuzumab, cetuximab, panitumumab, alirocumab, durvalumab, nimotuzumab, daratumumab, atezolizumab, sintilimab, toripalimab, camrelizumab, tislelizumab, durvalumab, nivolumab, and pembrolizumab. Optionally, the second therapeutic agent is selected from decitabine, gemcitabine, cisplatin, carboplatin, oxaliplatin, adriamycin, liposomal doxorubicin, taxol, docetaxel, trametinib, binimetinib, cobimetinib, durvalumab, atezolizumab, sintilimab, toripalimab, camrelizumab, tislelizumab, nivolumab, and pembrolizumab. Optionally, the second therapeutic agent is docetaxel, liposomal doxorubicin, cobimetinib, pembrolizumab, or decitabine. Optionally, the second therapeutic agent is cobimetinib.

In addition, the drug substances from which the second therapeutic agent is selected may be slightly different in names due to different translations, but they still refer to one drug substance, for example: cobimetinib may be translated into Chinese as Ka Bi Ti Ni or Kao Bi Ti Ni.

The term "inhibition" as used herein refers to a reduction in the baseline activity of a biological activity or process.

Technical and scientific terms used herein without specific definition have the meaning commonly understood by those skilled in the art to which the invention pertains.

Figure 6:
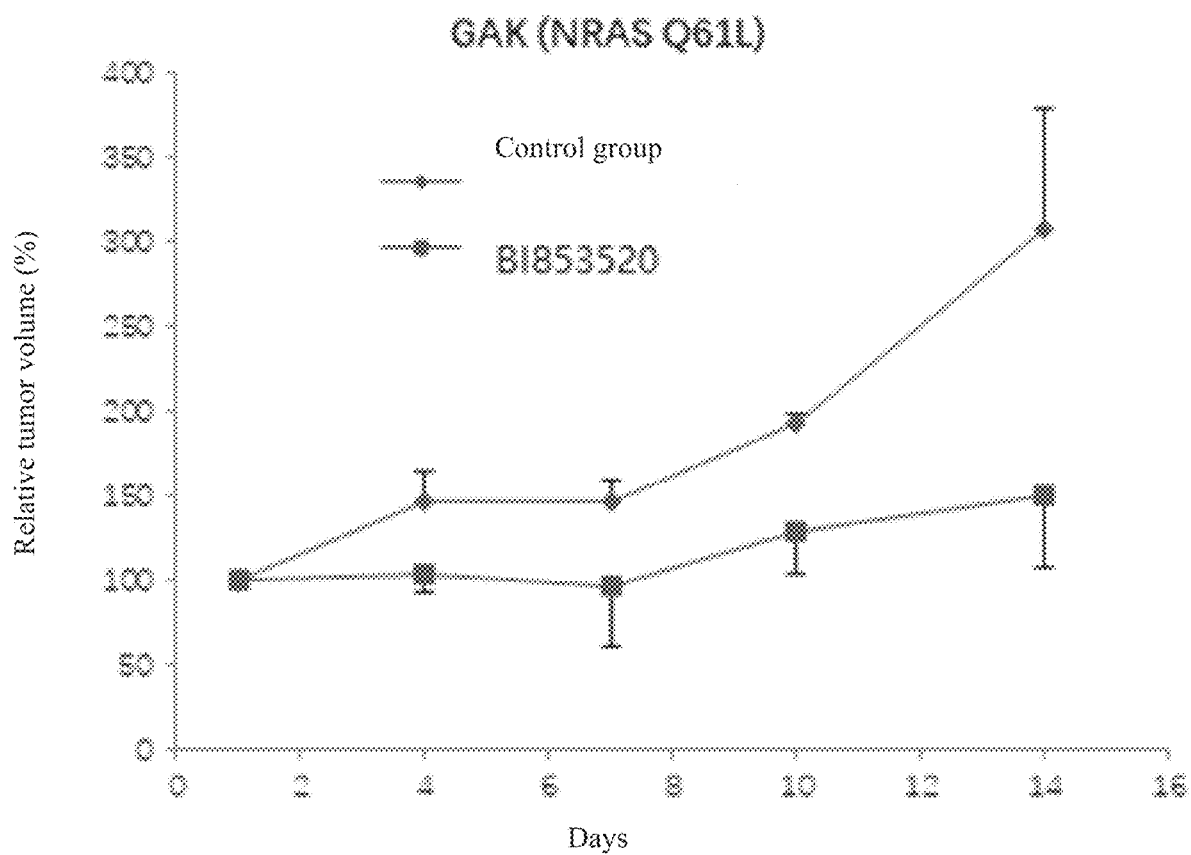

FIG. 6 shows GAK tumor growth kinetics. It illustrates that in the GAK model, daily treatment with BI 853520 delayed tumor growth compared to the control group.

Figure 7:
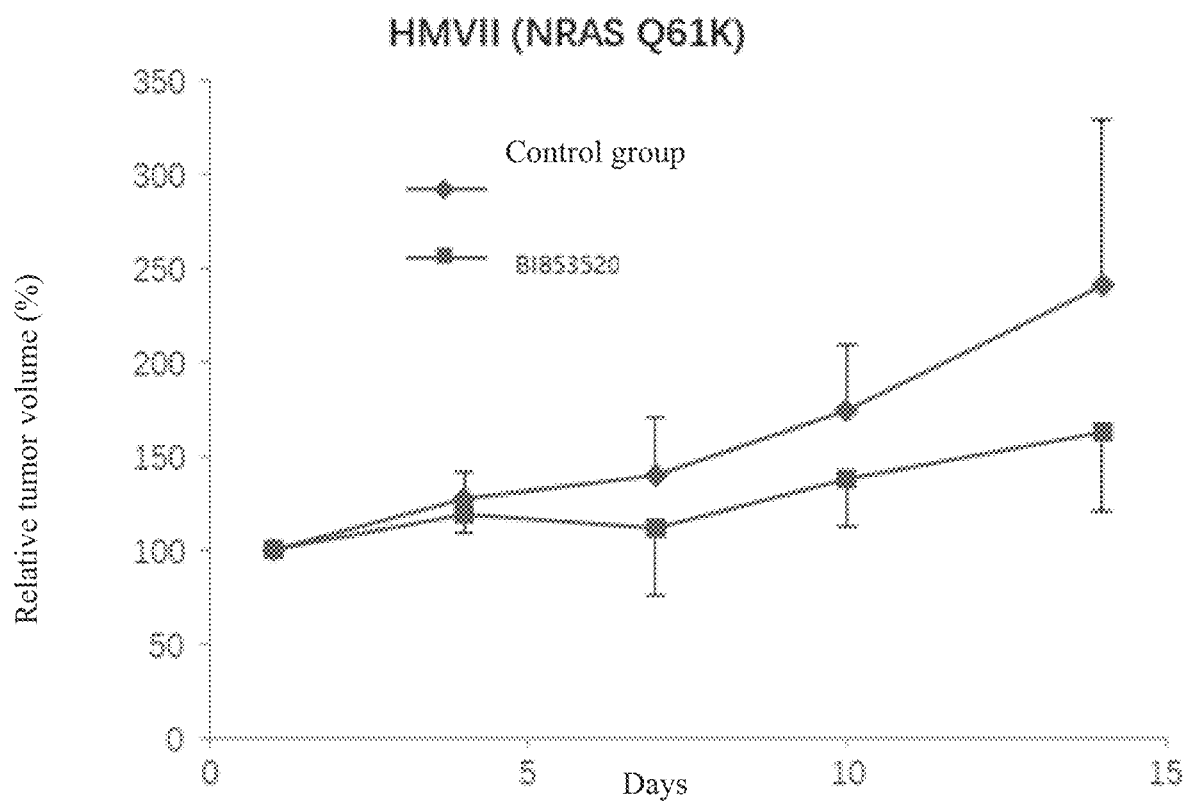

FIG. 7 shows HMVII tumor growth kinetics. It illustrates that in the HMVII model, daily treatment with BI 853520 delayed tumor growth compared to the control group.

DETAILED DESCRIPTION OF THE INVENTION

The following examples are provided to further illustrate the present disclosure. It should be understood that these examples are only used to illustrate the present disclosure and not to limit the scope of the present disclosure.

The experimental methods without specific conditions in the following examples can be carried out according to the conventional conditions of this type of reaction or according to the conditions suggested by the manufacturers.

The experimental materials and reagents used in the following examples can be obtained from commercial sources unless otherwise specified.

The meanings of the abbreviations used in the examples are as follows:

ATCC American Type Culture Collection
$CO_2$ Carbon dioxide
d Days
FCS Fetal Calf Serum
FBS Fetal Bovine Serum
g Gram
kg Kilograms
l Liter
mg Milligram
ml Milliliter
l Microliter
mM Millimole
$mm^3$ Cubic millimeter
GLP Good Laboratory Practice
h Hours
MCB Master Cell Bank
mean Arithmetic average
MTD Maximum tolerated dose
n Sample number
PBS Phosphate Buffered Saline
RPMI 1640 RPMI 1640 Medium
p.o. peros
qd Daily
q7d Every 7 days (once a week)
s.c. Subcutaneous
SD Standard deviation
TGI Tumor Growth Inhibition
WCB Working Cell Bank
$V_{rel}$ Relative Tumor Volume (relative to Day 1)

Example 1: Correlation Between Antitumor Effect of BI853520 and NRAS

1. Materials and Method:
1.1. DNA Construction and Retrovirus Production

Retroviral constructs expressing NRAS-G12D, KRAS4A-G12D, KRAS4B-G12D, and NRAS-G12D-C181S as N-terminal GFP fusion proteins were prepared according to a method as described in Cuiffo B, Ren R. *Palmitoylation of oncogenic NRAS is essential for leukemogenesis. Blood.*, 2010, 115: 3598-605, and Parikh C, Subrahmanyam R, Ren R. *Oncogenic NRAS, KRAS, and HRAS exhibit different leukemogenic potentials in mice. Cancer Res.*, 2007, 67: 7139-46. Retroviruses were prepared by using Bosc23 cells and the titre determination was performed by the method described in Parikh C, Subrahmanyam R, Ren R. *Oncogenic NRAS, KRAS, and HRAS exhibit different leukemogenic potentials in mice. Cancer Res.*, 2007, 67: 7139-46.

1.2. Cell Culture and Retroviral Transduction

The Ba/F3 cell line was obtained from ATCC in 2009, and cultured according to a method described in Zhang X Ren R. *Bcr-abl efficiently induces a myeloproliferative disease and production of excess interleukin-3 and granulocyte-macrophage colony-stimulating factor in mice: A novel model for chronic myelogenous leukemia. Blood.*, 1998, 92: 3829-40. Growth factor-dependent BA/F3 cells were cultured in RPMI 1640 including 10% FBS and supplemented with 15% WEHI-3 conditioned medium or recombinant IL-3 (Roche) as a source of IL-3 at a final concentration of 1 ng/ml. BA/F3 cells were transduced with retrovirus according to a method as described in Parikh C, Subrahmanyam R, Ren R. *Oncogenic NRAS, KRAS, and HRAS exhibit different leukemogenic potentials in mice. Cancer Res.*, 2007, 67: 7139-46 and Fredericks J, Ren R. *The role of RAS effectors in BCR/ABL induced chronic myelogenous leukemia. Front Med China.*, 2013, 7: 452-61. Upon receipt of the original stock, cells were expanded and frozen at a low passage rate (<3). Frozen cells were thawed and used in this study, with cell passages limited to 15 for all experimental procedures. All cells were tested regularly to ensure freedom and maintenance in a normal state of *mycoplasma*.

1.3. Materials

BI853520: synthesized according to the method in the patent WO2010058032.

1.4. Antiproliferative Test $NRAS^{G12D}$-transfected Ba/F3 (Ba/F3-N) or $KRAS^{G12D}$-transfected Ba/F3 (Ba/F3-N) cells were seeded into 96-well cell culture cluster plate in 100 μL of medium at a density of 5,000 cells per well. BI853520 was diluted 3-fold with RPMI 1640 at 9 points, and added according to the volume of each well, starting at 10 μmol/L to reach a 3-fold concentration gradient (final solvent concentration <1/1000). PD0325901 was used as a positive control. After 48 hours of incubation, cell viability was measured using CellTiter Glo (Promega). Luminescence was detected using an Envision plate reader (PerkinElmer). The calculation method of Z factor was as described in Zhang J H, Chung T D Y, Oldenburg K R. *A simple statistical parameter for use in evaluation and validation of high throughput screening assays. J Biomol Screen.*, 1999, 4: 67-73, and the following analysis only used data with Z factor >0.6. Dose-response curves were fitted based on the relative percentage of viable cells in nonlinear fitness (curve fitting) using GraphPad Prism® 6 software (www.graphpad.com/scientific-software/prism/). The internal software analysis "non-linear regression (curve fitting)" and the equation "log (inhibitor) vs. slope of response variable" were used for data analysis and $IC_{50}$ calculation.

2. Statistical Analysis:

GraphPad Prism® 6 software and Student's t-test were used for statistical data analysis. Statistically significant difference threshold was set at P=0.05.

Figure 1:
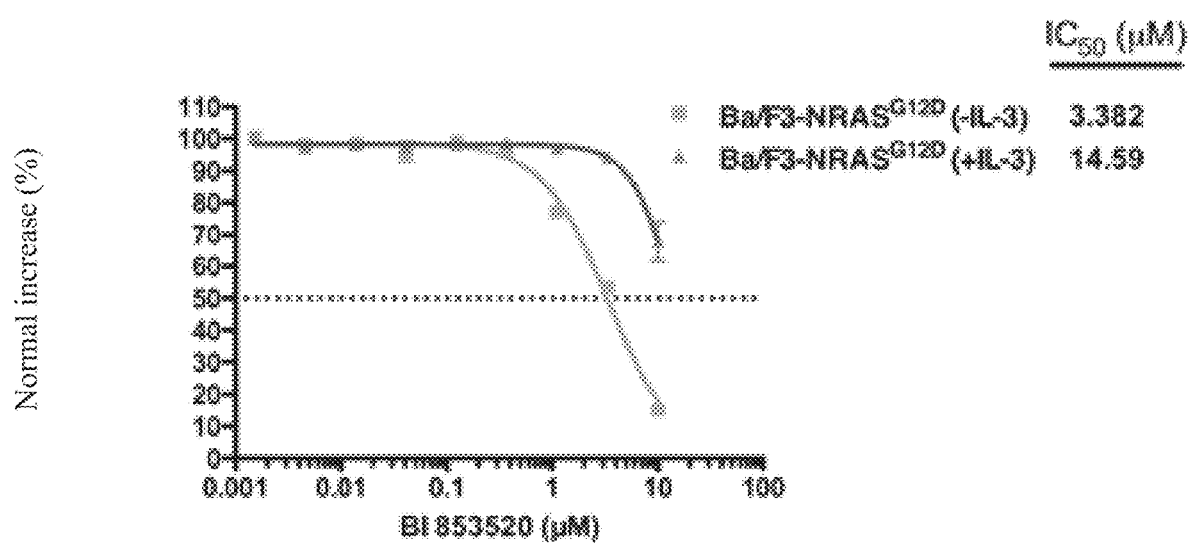
FIG. 1 shows influence of IL-3 on the antiproliferative effect of BI 853520 in the Ba/F3-NRAS$^{G12D}$ cell line. It illustrates that for BI853520, the IC$_{50}$ was increased from 3.4 to M after addition of IL-3 in NRAS$^{G12D}$-transfected Ba/F3 cell line (increased by more than 4-fold). GraphPad Prism 6 software and Student's t-test were used for statistical data analysis. Statistically significant difference threshold was set at P=0.05.

3. Results:

Ba/F3 is a murine marrow-derived cell line depending on IL-3 for survival and proliferation, and has been successfully used in high-throughput assays for kinase drug discovery. We tested this system with oncogenic RAS and found that oncogenic NRAS ($NRAS^{G12D}$) could convert Ba/F3 cells to being independent on IL-3. FIG. 1 and Table 1 show the antiproliferative effect of BI853520 on Ba/F3-$NRAS^{G12D}$ cell line with $IC_{50}$ value of 3.4 μM. The $IC_{50}$ increased more than 4-fold after the addition of IL-3, indicating that the inhibitory effect was related to NRAS.

TABLE 1

Influence of adding IL-3 or not on the antiproliferative effect of BI853520 in Ba/F3-$NRAS^{G12D}$ cell line

| | | $IC_{50}$ (μM) | |
| --- | --- | --- | --- |
| Cell line | Compound | − IL-3 | + IL-3 |
| Ba/F3-$NRAS^{G12D}$ | BI853520 | 3.4 | 15 |

Example 2: The Effect of BI853520 in a Mouse Model of Human Fibrosarcoma (Cell Line HT-1080)

Figure 2:
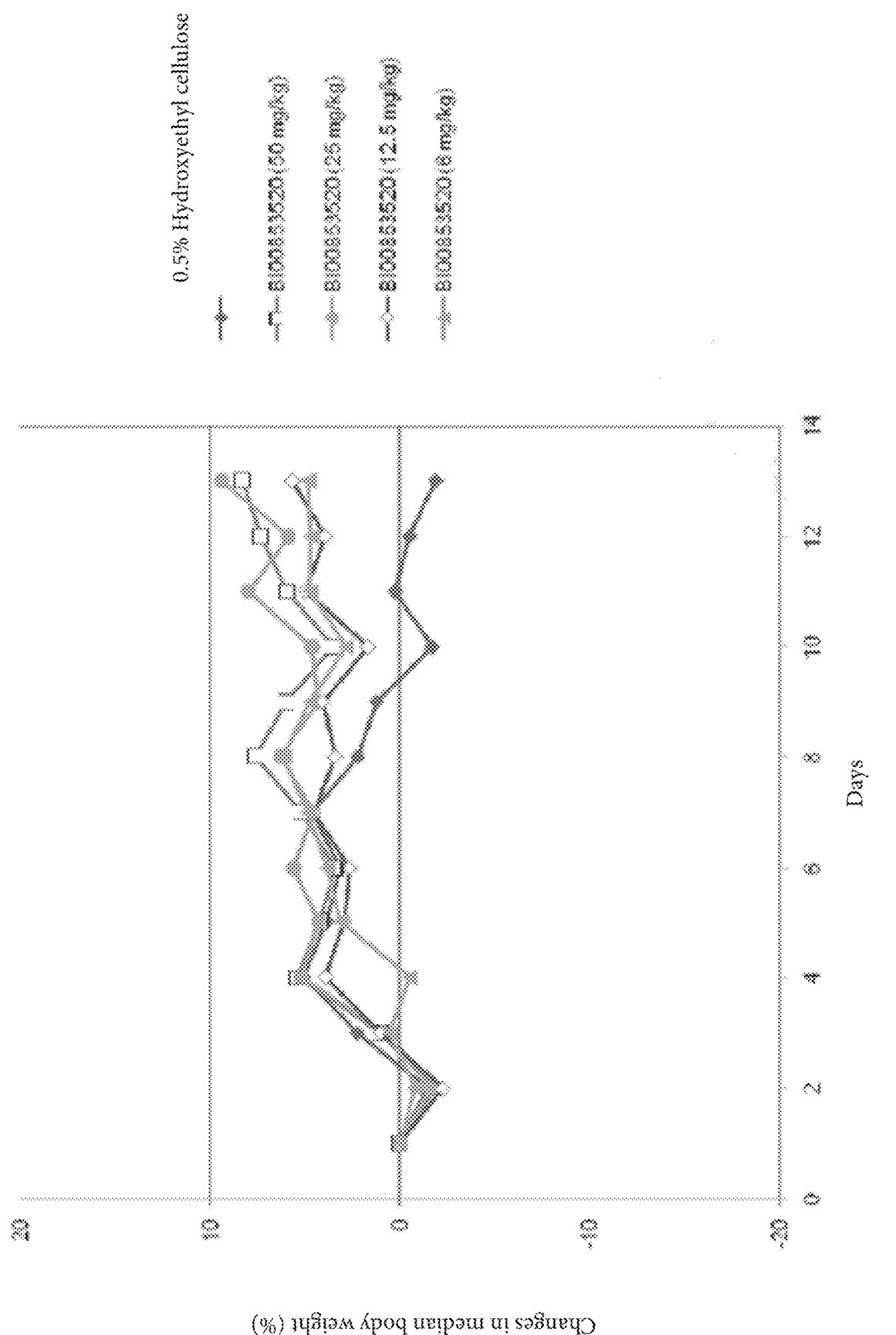
FIG. 2 shows changes in body weight. It illustrates that animals in the control group lost 1.9% body weight; animals treated with BI 853520 at 6 mg/kg had a median weight gain of 4.9% (p=0.9966 compared to the control group); animals treated with 853520 at 12.5 mg/kg had a median weight gain of 5.7% (p=0.9996 compared to the control group); animals treated with BI 853520 at 25 mg/kg had a median weight gain of 9.4% (p=1.0000 compared to the control group); and animals treated with BI 853520 at 50 mg/kg had a median weight gain of 8.3% (p=0.999 compared to the control group).
Figure 3:
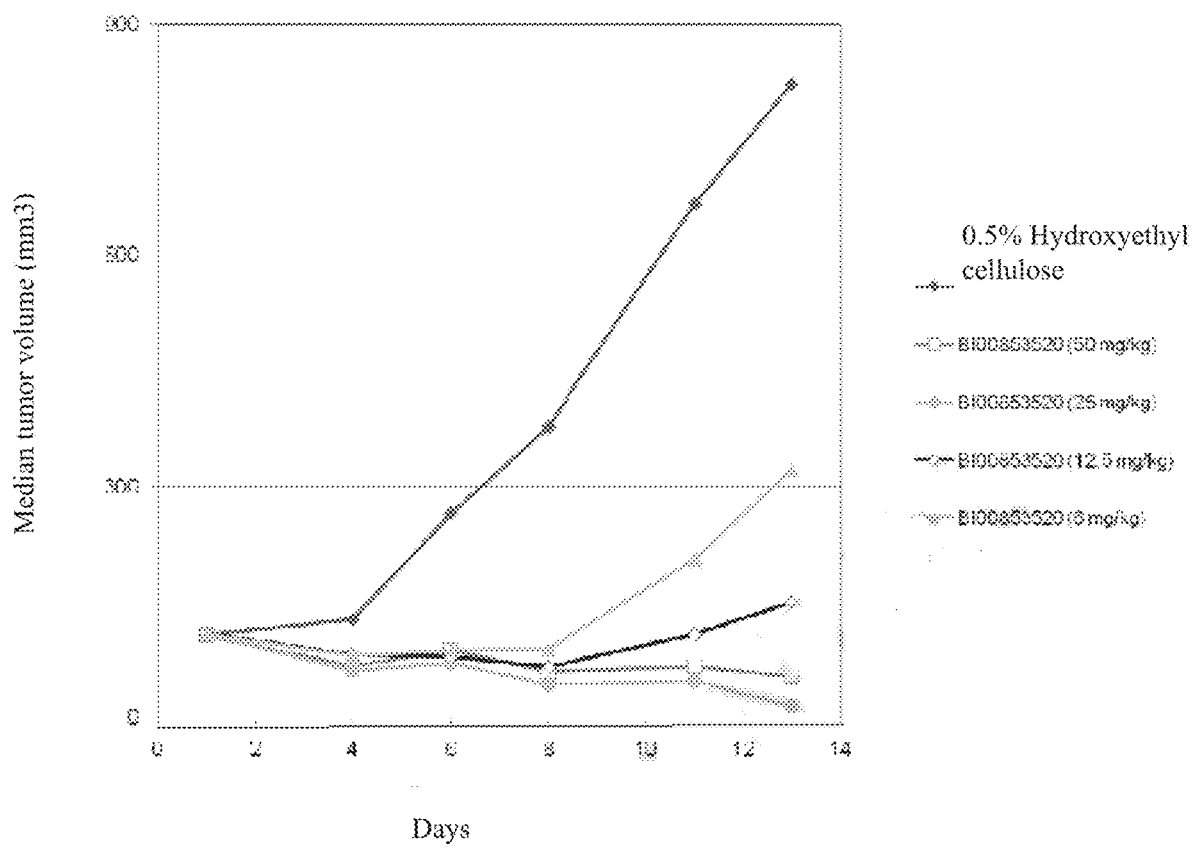
FIG. 3 shows HT-1080 tumor growth kinetics. It illustrates that on day 13, the median tumor volume of the control group was 823 mm$^3$; the median tumor volume of the group treated with BI 853520 at 6 mg/kg was 322 mm$^3$; the median tumor volume of the group treated with BI 853520 at 12.5 mg/kg was 149 mm$^3$; the median tumor volume of the group treated with BI 853520 at 25 mg/kg was 15 mm$^3$; and the median tumor volume of the group treated with BI 853520 at 50 mg/kg was 322 mm$^3$.

1. Materials and Method:
1.1. Design of Research
Treatment began when the median tumor volume was between 70-130 mm³.
10 mice in the control group, and 7 mice in the treatment group.
Oral gavage once daily.
Control: 0.5% hydroxyethyl cellulose
BI 853520: 50 mg/kg, 25 mg/kg, 12.5 mg/kg, 6 mg/kg,
Tumor volume was measured 3 times a week and body weight was monitored daily.
Evaluation of treatment outcome was based on absolute volume of individual tumors.
Tolerability was assessed based on changes in body weight.
1.2. Materials
BI853520: synthesized according to the method in the patent WO2010058032. The dry powder was suspended in 0.5% hydroxyethyl cellulose to obtain the desired concentration for each assay. The pH of this formulation was 3.5.
HT-1080 cells: HT-1080 cells carrying NRAS, CDKN2A and IDH1 gene mutations were obtained from ATCC (CRL-121). Cells were grown in T175 tissue culture flasks with DMEM+Glutamax supplemented with 10% heat-inactivated fetal bovine serum as medium. Cells were cultured at 37° C. and 5% $CO_2$ in humidified air.
Mice: Athymic female BomTac, approximately 6-week-old NMRI-Foxn1$^{nu}$ mice were purchased from Taconic, Denmark. After arriving in the animal room, mice were acclimated to the new environment for at least 3 days before being used for assay. The animals were housed under standard conditions (temperature 21.5±1.5° C. and 55±10% humidity) with 5 mice in each group. A standard diet and autoclaved tap water were provided for ad libitum feeding. A Datamars® T-IS 8010 FDX-B transponder implanted subcutaneously in the neck region and a LabMax® II fixed reader were used to identify each mouse. The cage card showed study number, animal identification number, compound and dose level, route of administration, and dosing schedule for animals throughout the assay.
1.3. Random Establishment of Tumors:
To establish subcutaneous tumors, HT-1080 cells were harvested by trypsinization, centrifuged, washed and suspended in ice-cold PBS+1×10⁸ cells/ml. Then 100 μl of cell suspension containing 1×10⁷ cells was injected subcutaneously into the right flank of nude mice (1 site per mouse). When tumors were established and reached a diameter of 5-8 mm (7 days after cell injection), mice were randomly assigned to the treatment group and the control group.
1.4. Dosing:
BI853520 was suspended in 0.5% hydroxyethyl cellulose, which was administered intragastrically through gavage needle every day, and the dosage was 10 mL/Kg.
1.5. Monitoring Tumor Growth and Side Effects:
Tumor diameters were measured with calipers three times a week (Monday, Wednesday, and Friday). The volume of each tumor [in mm³] was calculated according to the equation, "tumor volume=length×diameter²×π/6". To monitor the side effects of the treatment, the mice were checked daily for abnormalities and their body weights were measured daily. Animals were sacrificed at the end of the study (approximately two weeks after the start of treatment). During the study, animals with tumor necrosis or tumors larger than 2000 mm³ were sacrificed ahead of schedule for ethical reasons.
2. Statistical Analysis:
At the end of the assay on day 13, statistical evaluation of tumor volume and body weight parameters was performed. Absolute tumor volume and percent change in body weight (referenced to initial weight on day 1) were used. A non-parametric approach was used, and the number of observations, median, minimum and maximum values were calculated. For a quick overview of possible treatment effects, the median tumor volume for each treatment group T and the median tumor volume for the control group C were used to calculate the TGI from day 1 to day d:

$$TGI=100\times[(C_d-C_1)-(T_d-T_1)]/(C_d-C_1)$$

wherein, $C_1$, $T_1$=median tumor volume in control and treatment groups at the start of the assay (day 1).
$C_d$, $T_d$=median tumor volume in control and treatment groups at the end of the assay (day 13).
Each dose of test compound was compared to the control group using a one-sided descending wilcoxon test, taking reduction in tumor volume as a treatment effect and weight loss as a side effect. The P-values for tumor volume (the efficacy parameter) were compared and adjusted for multiple times according to Bonferroni-Holm, while the P-values for body weight (the tolerance parameter) were not adjusted so as not to overlook possible side effects. Significance level was fixed at α=5%. A p-value (adjusted) of less than 0.05 was considered to show a statistically significant difference between groups, and 0.05≤p-value<0.10 was considered as an indicative difference. Statistical evaluations were performed using the software packages SAS version 9.2 (SAS Institute Inc., Cary, NC, USA) and Proc StatXact® version 8.0 (Cytel Software, Cambridge, MA, USA).
3. Results:
3.1. During the test period, animals in the control group lost 1.9% body weight (FIG. 2, Table 2), and on day 13, their median tumor volume reached 823 mm³ (FIG. 3, Table 3).
3.2. Treatment with BI 853520 at 50 mg/kg once daily resulted in a TGI of 107% (p=0.0002), and tumor shrinkage was observed in all animals (FIG. 3, Table 3). The median body weight of the animals increased by 8.3% (p=0.999 compared to the control group) (FIG. 2, Table 2).
3.3. Treatment with BI 853520 at 25 mg/kg once daily resulted in a TGI of 113% (p=0.0002) and tumor shrinkage in 6 animals (FIG. 3, Table 3). The median body weight of the animals increased by 9.4% (p=1.0000 compared to the control group) (FIG. 2, Table 2).

3.4. Treatment with BI 853520 at 12.5 mg/kg once daily resulted in a TGI of 94% (p=0.0002) and tumor shrinkage in 2 animals (FIG. 3, Table 3). The median body weight of the animals increased by 5.7% (p=0.9996 compared to the control group) (FIG. 2, Table 2).

Figure 5:
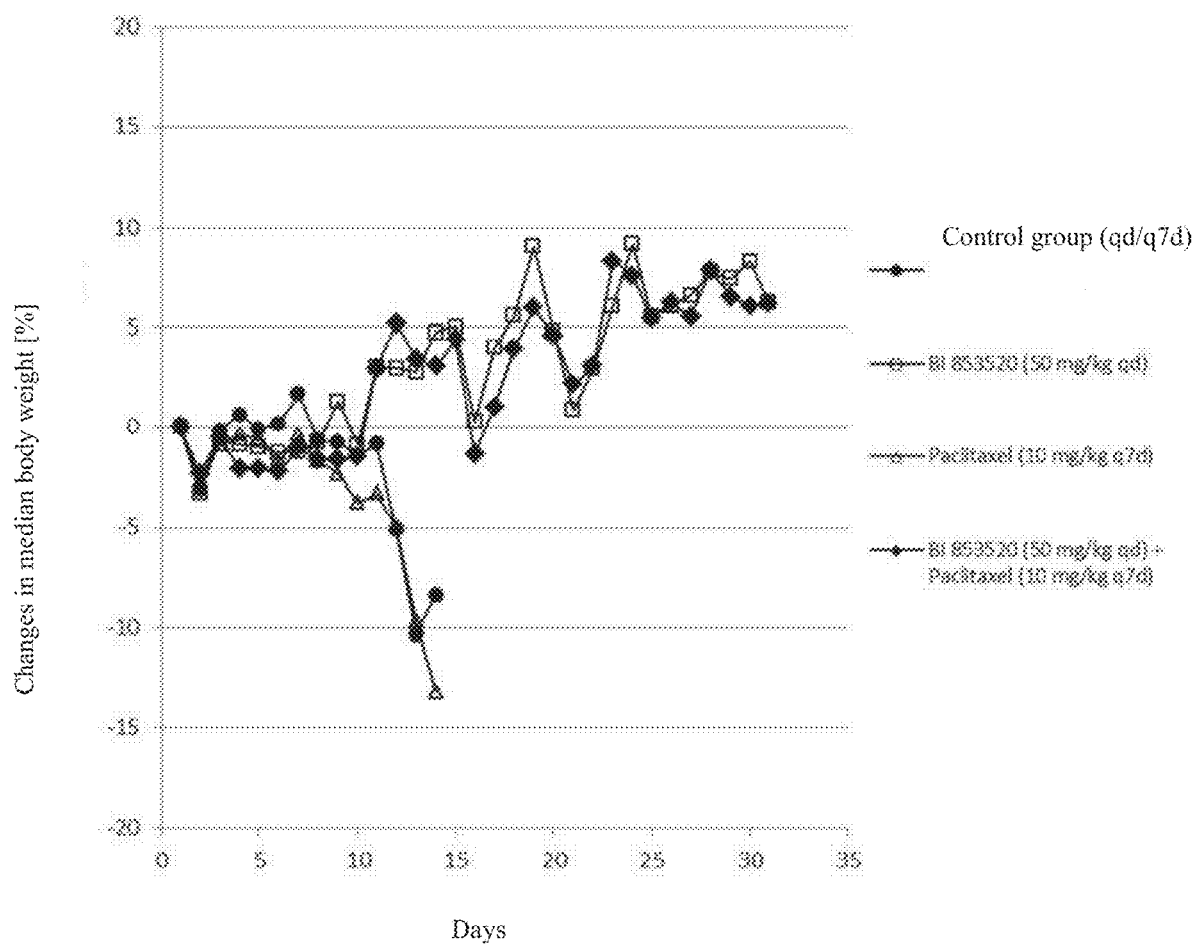
FIG. 5 shows changes in body weight. It illustrates that animals in the control group had a 10.3% reduction in the median body weight, and compared to the control group, animals treated with 50 mg/kg BI 853520 daily had a 2.8% increase in the median body weight, animals treated with 10 mg/kg paclitaxel once a week had a 9.7% reduction in the median body weight, and animals treated with the combination therapy of 50 mg/kg BI 853520 once daily with 10 mg/kg paclitaxel once a week had a 3.5% increase in the median body weight.

3.5. Treatment with BI 853520 at 6 mg/kg once daily resulted in a TGI of 70% (p=0.0004) and tumor shrinkage in 1 animal (FIG. 5, Table 3). The median body weight of the animals increased by 4.9% (p=0.9966 compared to the control group) (FIG. 2, Table 2).

TABLE 2

Median weight change at the end of the assay

| Dosage (mg/Kg) | Dosing schedule | Median weight change (%) |
|---|---|---|
| control group | qd | −1.9 |
| 50 | qd | +8.3 |
| 25 | qd | +9.4 |
| 12.5 | qd | +5.7 |
| 6 | qd | +4.7 |

TABLE 3

Median tumor volume

| Dosage (mg/Kg) | Dosing schedule | Median tumor volume (mm$^3$) | Tumor shrinkage [X/7] | TGI [%] |
|---|---|---|---|---|
| control group | qd | 823 | — | n.a |
| 50 | qd | 54 | 7 | 107 |
| 25 | qd | 15 | 6 | 113 |
| 12.5 | qd | 149 | 2 | 94 |
| 6 | qd | 322 | 1 | 70 |

In the human HT-1080 fibrosarcoma model, BI 853520 demonstrated statistically significant antitumor activity at all dose levels, and regression was observed in all the treatment groups; reduction in tumor volume was observed in all animals at the highest dose level. In previous studies, the highest daily dose was 100 mg/kg without limiting toxicity. Thus, significant efficacy was obtained at a dose at least 16 times lower than the MTD (6 mg/kg).

Example 3: Antitumor Activity of BI 853520 in a Subcutaneous Xenograft Mouse Model Derived from the Human Esophageal Cancer Cell Line KYSE-270 in NMRI Nude Mice 1. Materials and Methods 1.1. Model: Subcutaneous xenograft of human esophageal cancer cell line KYSE-270 in NMRI nude mice.

1.2. Test compound: BI853520: synthesized according to the method in patent WO2010058032.

1.3. Cells: KYSE-270 is an esophageal cancer cell line (Public Health England, catalog number: 94072021). Cells were cultured in T175 tissue culture flasks containing 5% $CO_2$ at 37° C. The medium was RPMI 1640+HAM F12 (1:1) supplemented with 2% FCS and 2 mM Glutamax. Passage was performed three times a week at a ratio of 1:2.

1.4. Mice: Mice were 8 to 10 week old female mice (BomTac: NMRI-Foxn1$^{nu}$) purchased from Taconic®, Denmark. Upon arrival in the animal room, the mice were allowed to acclimate for at least 5 days before being used for assay. The animals were housed under standard conditions (temperature: 21.5±1.5° C., humidity: 55+10%), 7 to 10 mice for each group. A standard diet and autoclaved tap water were provided for ad libitum feeding. A subcutaneous microchip implanted under isoflurane anesthesia was used to identify each mouse. The cage card showed study number, animal identification number, compound and dose level, route of administration, and dosing schedule for animals throughout the assay.

1.5. Random establishment of tumors: To establish subcutaneous tumors, KYSE-270 cells were harvested by centrifugation, washed and resuspended in PBS+5% FCS at a concentration of 5×10$^7$ cells/ml. Then 100 l of cell suspension containing 5×10$^6$ cells was injected subcutaneously into the right flank of mice (1 site per mouse). When tumors were well established and reached a volume of 94 to 252 mm$^3$, mice were randomly assigned to the treatment group and the control group (13 days after cell injection).

1.6. Administration: BI 853520 was suspended in 0.5% hydroxyethyl cellulose, which was administered intragastrically through gavage needle every day, and the dosage was 10 mL/Kg body weight. Paclitaxel was dissolved in saline (0.9% NaCl), which was administered intravenously in a volume of 10 ml/kg body weight. The suspension of BI853520 could be used for up to 7 days. Paclitaxel solution was stored at 6° C. and used for up to 14 days.

1.7. Monitoring tumor growth and side effects: Tumor diameters were measured with calipers three times a week. The volume [mm$^3$] of each tumor was calculated according to the equation "tumor volume=length×diameter$^2$×π/6". To monitor the side effects of the treatment, the mice were checked daily for abnormalities and their body weights were measured three times a week. For ethical reasons, animals with tumors larger than 1.5 cm in diameter, ulcerated tumors, or 20% body weight loss were euthanized.

2. Statistical Analysis:

Statistical assessment of tumor volume and body weight on day 13 was performed. Animal number 1 (control group) was excluded from the statistical evaluation because of weight loss and had to be euthanized early (day 9). Measured tumor volume was used as the target variable in the statistical analysis. The number of animals and the median, minimum and maximum tumor volumes in each group were calculated. For a quick overview of possible treatment effects, the median tumor volume for each treatment group T and the median tumor volume for the control group C were used to calculate TGI:

$$TGI=100\times[(C_d-C_1)-(T_d-T_1)]/(C_d-C_1)$$

wherein, $C_1$, $T_1$=median tumor volume in control and treatment groups at the start of the assay (day 1).

$C_d$, $T_d$=median tumor volume in control and treatment groups at the end of the assay (day 13).

The wilcoxon test was used for comparison. For body weight, the percent change relative to initial body weight on day 1 was used as the target variable for statistical analysis. The number of animals, and the median, minimum and maximum weight changes in each group were calculated.

One-sided test to compare all treatment groups with control group was performed for observing:
reduction in tumor volume (inhibition of tumor growth, efficacy parameter) and
reduction in weight changes (weight loss, tolerance parameters).

Within each subtopic, p-values for the efficacy parameter were compared and adjusted for multiple times according to Bonferroni-Holm. The p-value for the tolerance parameter was kept constant so as not to overlook possible side effects. Significance level was fixed at α=5%. A p-value (adjusted) of less than 0.05 was considered to show a statistically significant difference between groups, and 0.05≤p-value<0.10 was considered as an indicative difference. Statistical evaluations were performed using the SAS software package version 9.4 (SAS Institute Inc., Cary NC, USA).

3. Results

Figure 4:
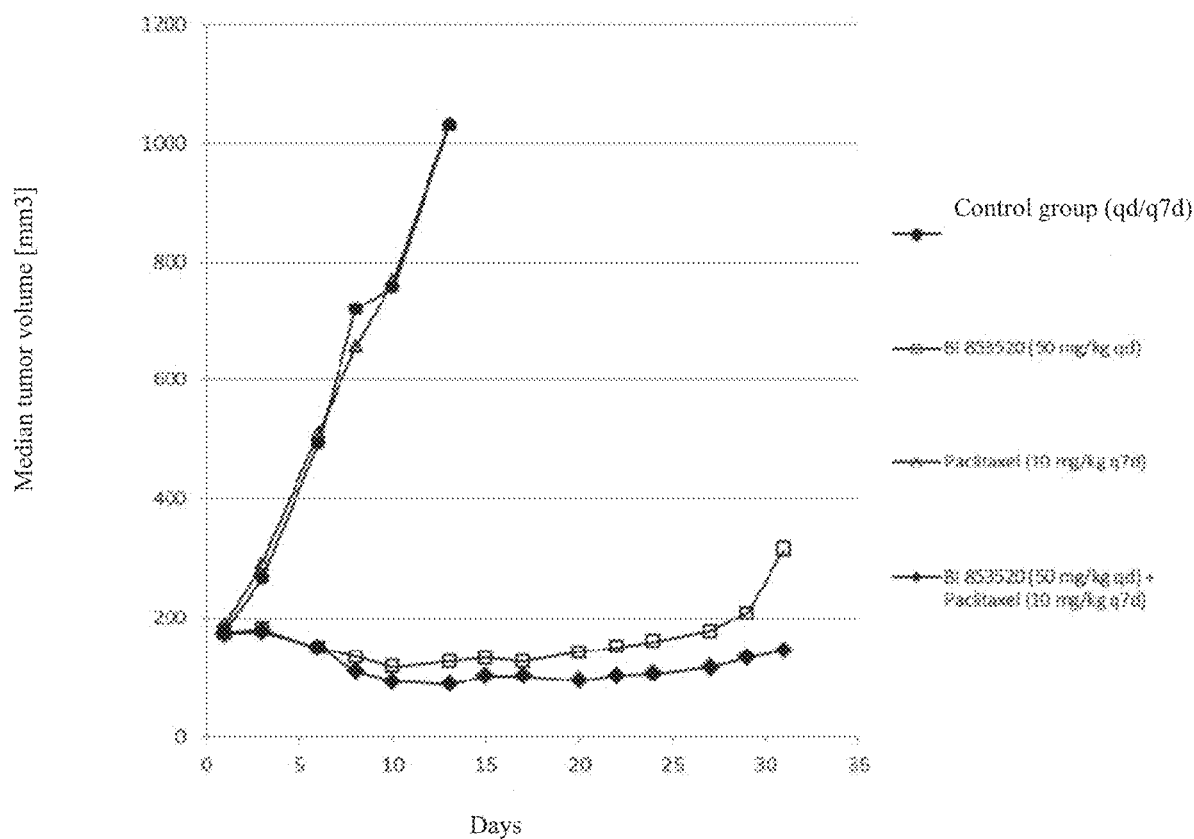
FIG. 4 shows KYSE-270 tumor growth kinetics, which illustrates the median tumor volume increased from 179 mm$^3$ to 1032 mm$^3$ in the control group. Compared to the control group, the median tumor volume of the group treated with 50 mg/kg BI 853520 per day decreased from 175 mm$^3$ to 126 mm$^3$. Treatment with 10 mg/kg paclitaxel once a week had no effect on tumor growth, in which the median tumor volume increased from 190 mm$^3$ to 1033 mm$^3$. The combination therapy of 50 mg/kg BI 853520 once a day with 10 mg/kg paclitaxel once a week significantly delayed tumor growth, with the median tumor volume decreased from 173 mm$^3$ to 87 mm$^3$.

Tumor Volume and Body Weight:

By day 13, the median tumor volume in the control group increased from 179 mm³ to 1032 mm³ (FIG. 4). The median body weight of control animals decreased by 10.3% (FIG. 5, Table 4). On day 9, one animal had to be euthanized due to severe weight loss.

Daily treatment with 50 mg/kg BI 853520 significantly delayed tumor growth (median TGI=106%, p=0.0003) compared to the control group (FIG. 5, Table 4). On day 13, 6 of 7 tumors had shrunk (Table 4). The median body weight of the animals increased by 2.8%, which was not significantly different from the control group (p=0.9999) (FIG. 5, Table 4).

Treatment with 10 mg/kg paclitaxel once a week had no effect on tumor growth (median TGI=2%, p=0.3788) compared to the control group (FIG. 4, Table 4). On day 13, none of the animals had tumor shrinkage (Table 4). The median body weight of the animals decreased by 9.7%, which was not significantly different from the control group (p=0.7320) (FIG. 5, Table 4).

Combination therapy of BI 853520 at 50 mg/kg once daily and 10 mg/kg paclitaxel once a week significantly delayed tumor growth (median TGI=110%, p=0.0003) compared to the control group (FIG. 4, Table 4). On day 13, all animals had tumor shrinkage (Table 4). The median body weight of the animals increased by 3.5%, which was not significantly different from the control group (p=1.0000) (FIG. 5, Table 4).

TABLE 4

TGI, tumor shrinkage and body weight change in each group (day 13)

| Compound | Dosage (Dosing Schedule) | TGI (%) | Tumor shrinkage [x/y] | Change in median weight (%) |
|---|---|---|---|---|
| Control group | —(qd + q7d) | | | −10.3 |
| BI853520 | 50 mg/Kg (qd) | 106 | 6/7 | +2.8 |
| Paclitaxel | 10 mg/Kg (q7d) | 2 | 0/7 | −9.7 |
| BI853520 + Paclitaxel | 50 mg/Kg (qd) + 10 mg/Kg (q7d) | 110 | 7/7 | 3.5 |

4. Conclusion

In a subcutaneous xenografted model of the human esophageal cancer cell line KYSE-270, statistically significant inhibition of tumor growth was observed in the treatment group with 50 mg/kg BI 853520 and the treatment group with 50 mg/kg BI 853520 in combination with 10 mg/kg paclitaxel, and both were well tolerated.

Example 4: Tumor Growth Inhibitory Effect of BI 853520 on HMVII and GAK CDX Models (Melanoma Models with an NRAS Mutation)

1. Materials and Methods 1.1. Test compound: BI853520, which was synthesized according to the method in the patent WO2010058032. BI853520 was formulated with 0.5% hydroxyethyl cellulose (Ashland).

1.2. Cells: The melanoma cell line GAK was purchased from JCRB Cell Bank, and HMVII cells were purchased from Sigma. GAK originated in the inguinal lymph nodes of patients with vaginal melanoma, whereas HMVII originated in primary vaginal melanoma. GAK and HMVII cells were cultured in tissue culture flasks containing 5% $CO_2$ at 37° C. The media were Ham's F12 containing 10% heat-inactivated FBS and Ham's F10 containing 15% FBS, respectively. All media were supplemented with 100 U/mL penicillin, 100 mg/mL streptomycin, and 2 mM GlutaMAX. All cell culture reagents were purchased from GIBCO.

Both HMVII and GAK cell lines carried an NRAS mutation at the Q61 position. HMVII (NRAS$^{Q61K}$) and GAK (NRAS$^{Q61L}$)

1.3. Mice: 4-week-old female balb/c nude mice (purchased from Beijing Vital River Laboratory Animal Technology Co., Ltd.). After arriving in the animal room, the mice were allowed to acclimate to the new environment for at least 2 weeks before being used for assay. The animals were housed under standard conditions (temperature: 21.5±1.5° C., humidity: 55±10%). A Standard diet and autoclaved tap water were provided ad libitum. All animal care and experimental procedures were performed in accordance with the animal care ethics guidelines approved by the Medical Ethics Committee of Beijing Cancer Hospital and Research Institute.

1.4. Random establishment of tumors:

To establish subcutaneous tumors, HMVII and GAK cells were harvested by trypsinization, centrifuged, washed and resuspended in ice-cold PBS+5% FCS. Then 100 l of the cell suspension containing 5×10⁶ cells was injected subcutaneously into the right flank of nude mice (1 site per mouse). When tumors were well established and reached a median volume of approximately 400-600 mm³, mice were randomly assigned to the treatment group and the control group.

1.5. Administration: BI 853520 was formulated in 0.5% hydroxyethyl cellulose, which was intragastrically administered through gavage needle every day, and the dosage was 10 mL/Kg body weight.

1.6. Monitoring tumor growth:

Tumor diameters were measured twice a week with calipers. The volume [mm³] of each tumor was calculated according to the equation "tumor volume=length×diameter²×π/6". Animals were sacrificed at the end of the study (approximately two weeks after the start of treatment). During the study, animals with necrotic tumors or tumors exceeding 2000 mm³ in size were sacrificed for ethical reasons.

2. Statistical Analysis:

Tumor volumes were statistically assessed at the end of the assay. For tumor volume, relative values were used.

The number of observations, and the median, minimum and maximum tumor volumes were calculated. For a quick overview of possible treatment effects, the following metrics were calculated:

Relative tumor volume: (T/C)

$$T/C = 100 * \frac{T_d}{C_d};$$

TGI from day 1 to day d:

$$TGI = 100 \times [(C_d - C_1) - (T_d - T_1)]/(C_d - C_1)$$

wherein, $C_1$, $T_1$=mean relative tumor volume in control and treatment groups at the start of the assay (day 1);

C_d, T_d=mean relative tumor volume in control and treatment groups at the end of the assay (day d).

Statistical evaluation was performed using the Student's t-test function in Microsoft Excel, using two-tailed distribution and two-sample equal variance type.

The significance level was fixed at α=5%. A p-value (adjusted) of less than 0.05 was considered to show a significant difference between treatment groups, and 0.05≤p-value<0.10 was considered as an indicative difference.

3. Results

In the GAK model, daily treatment with BI 853520 delayed tumor growth (median TGI=80%, p=0.03) compared to the control group (FIG. 6, Table 5).

In the HMVII model, daily treatment with BI 853520 delayed tumor growth (median TGI=60%, p=0.17) compared to the control group (FIG. 7, Table 5).

TABLE 5

Mean tumor volume, mean TGI and P-value based on relative tumor volume on day 14

| Group | Cell line | Scheme | Mean tumor volume [mm³] | Mean TGI | P |
|---|---|---|---|---|---|
| A | HMVII | 0.5% hydroxyethyl cellulose | 1237 ± 733 (n = 3) | — | — |
| B | HMVII | BI853520 50 mg/kg (during the 1st week) 25 mg/kg (during the 2nd week) | 671 ± 606 (n = 4) | 60% | 0.17 |
| C | GAK | 0.5% hydroxyethyl cellulose | 1387 ± 1180 (n = 3) | — | — |
| D | GAK | BI853520 50 mg/kg (during the 1st week) 25 mg/kg (during the 2nd week) | 548 ± 144 (n = 3) | 80% | 0.03 |

4. Conclusion

BI853520 can inhibit tumor growth in CDX models of HMVII and GAK (two melanoma models with an NRAS mutation).

All references mentioned herein are incorporated by reference in their entirety, as if each were individually listed. It should be understood that after reading the disclosure of the present invention, those skilled in the art can make various changes or modifications to the present invention, and these equivalent forms also fall within the scope defined by the appended claims of the present application.

What is claimed is:

1. A method of treating a melanoma having an NRAS mutation, comprising administering to an individual an effective amount of BI853520 or a pharmaceutically acceptable salt thereof thereby inhibiting the growth of the melanoma.

2. The method of claim 1, wherein the pharmaceutically acceptable salt thereof is BI853520 tartrate.

3. The method of claim 1, further comprising administering to the individual an effective amount of a second therapeutic agent.

4. The method of claim 1, further comprising a radiotherapy or a cell therapy.

5. The method of claim 3, wherein the second therapeutic agent comprises one or more of a chemotherapeutic agent, a targeted therapeutic agent, or an immunotherapeutic agent.

6. The method of claim 3, wherein the second therapeutic agent comprises one or more of nimustine, carmustine, lomustine, temozolomide, cyclophosphamide, isocyclophosphamide, glyfosfin, doxifluridine, Furtulon, fluorouraeil, mercaptopurine, azathioprine, tioguanine, floxuridine, tegafur, gemcitabine, decitabine, carmofur, hydroxyurea, methotrexate, UFT, capecitabine, ancitabine, thiotepa, actinomycin D, adriamycin, liposomal doxorubicin, daunorubicin, epirubicin, mitomycin, pingyangmycin, pirarubicin, valrubicin, idarubicin, irinotecan, harringtonine, camptothecin, hydroxycamptothecine, topotecan, vinorelbine (navelbine), taxol, taxotere, hycamtin, vinblastine, vincristine, vindesine, vindesine sulfate, vincaleukoblastine, teniposide, etoposide, elemene, atamestane, anastrozole, aminoglutethimide, letrozole, formestane, megestrol, tamoxifen, asparaginase, carboplatin, cisplatin, dacarbazine, oxaliplatin, eloxatin, Eloxatin (Ke Bo Ao Sha), mitoxantrone, procarbazine, docetaxel, gefitinib, erlotinib, icotinib, afatinib, osimertinib, crizotinib, ceritinib, alectinib, lapatinib, everolimus, palbociclib, ribociclib, apatinib, regorafenib, sorafenib, sunitinib, temsirolimus, lenvatinib, pazopanib, Alectinib (A Lei Ti Ni), axitinib, cabozantinib, trametinib, binimetinib, vemurafenib, dabrafenib, Cobimetinib (Ka Bi Ti Ni), vandetanib, bortezomib, palbociclib, lenalidomide, ixazomib, imatinib, dasatinib, bosutinib, ponatinib, ibrutinib, idelalisib, belinostat, romidepsin, vorinostat, olaparib, niraparib, denosumab, vismodegib, sonidegib, rucaparib, brigatinib, bicalutamide, enzalutamide, abiraterone, abemaciclib, apalutamide, aflibercept, azacitidine, bleomycin, chlorambucil, cytarabine, Asparaginase (Tian Dong Xian An Mei), epothilone, fludarabine, flutamide, mechlorethamine, paclitaxel, pemetrexed, raltitrexed, necitumumab, bevacizumab, ramucirumab, Ado-trastuzumab, pertuzumab, cetuximab, panitumumab, alirocumab, durvalumab, nimotuzumab, daratumumab, atezolizumab, sintilimab, toripalimab, camrelizumab, tislelizumab, nivolumab, or pembrolizumab.

7. The method of claim 3, wherein BI853520 or a pharmaceutically acceptable salt thereof and the second therapeutic agent are administered simultaneously.

8. The method of claim 4, wherein administration of BI853520 or a pharmaceutically acceptable salt thereof and the radiotherapy or the cell therapy are performed simultaneously.

9. The method of claim 6, wherein the second therapeutic agent is decitabine, gemcitabine, cisplatin, carboplatin, oxaliplatin, adriamycin, liposomal doxorubicin, taxol, docetaxel, trametinib, binimetinib, cobimetinib, durvalumab, atezolizumab, sintilimab, toripalimab, camrelizumab, tislelizumab, nivolumab, or pembrolizumab.

10. The method of claim 9, wherein the second therapeutic agent is docetaxel, liposomal doxorubicin, cobimetinib, pembrolizumab, or decitabine.

11. The method of claim 10, wherein the second therapeutic agent is cobimetinib.

12. The method of claim 3, wherein BI853520 or a pharmaceutically acceptable salt thereof and the second therapeutic agent are administered alternately.

13. The method of claim 3, wherein BI853520 or a pharmaceutically acceptable salt thereof and the second therapeutic agent are administered sequentially.

14. The method of claim 4, wherein administration of BI853520 or a pharmaceutically acceptable salt thereof and the radiotherapy or the cell therapy are performed alternately.

15. The method of claim 4, wherein administration of BI853520 or a pharmaceutically acceptable salt thereof and the radiotherapy or the cell therapy are performed sequentially.

* * * * *